(12) United States Patent
Ueyama et al.

(10) Patent No.: US 11,786,326 B2
(45) Date of Patent: Oct. 17, 2023

(54) TREATMENT APPARATUS

(71) Applicant: SONIRE THERAPEUTICS INC., Tokyo (JP)

(72) Inventors: Tsuyoshi Ueyama, Kariya (JP); Seisho Inada, Kariya (JP); Hideki Okuda, Kariya (JP)

(73) Assignee: SONIRE THERAPEUTICS INC., Tokyo (JP)

( * ) Notice: Subject to any disclaimer, the term of this patent is extended or adjusted under 35 U.S.C. 154(b) by 647 days.

(21) Appl. No.: 17/010,790

(22) Filed: Sep. 2, 2020

(65) Prior Publication Data

US 2020/0397519 A1    Dec. 24, 2020

Related U.S. Application Data

(63) Continuation of application No. PCT/JP2019/011487, filed on Mar. 19, 2019.

(30) Foreign Application Priority Data

Mar. 22, 2018  (JP) .................................. 2018-054209

(51) Int. Cl.
| | |
|---|---|
| *A61B 34/00* | (2016.01) |
| *A61B 34/35* | (2016.01) |
| *A61B 8/00* | (2006.01) |
| *B25J 9/16* | (2006.01) |
| *B25J 13/08* | (2006.01) |
| *A61N 7/02* | (2006.01) |
| *A61N 7/00* | (2006.01) |

(52) U.S. Cl.
CPC ............ *A61B 34/35* (2016.02); *A61B 8/4218* (2013.01); *A61B 34/77* (2016.02); *A61N 7/02* (2013.01); *B25J 9/1633* (2013.01); *B25J 13/085* (2013.01); *A61N 2007/0065* (2013.01)

(58) Field of Classification Search
CPC ................................. A61B 34/35; A61B 34/77
See application file for complete search history.

(56) References Cited

FOREIGN PATENT DOCUMENTS

| | | |
|---|---|---|
| JP | H0435660 A | 2/1992 |
| JP | H0884740 A | 4/1996 |

*Primary Examiner* — Joseph M Santos Rodriguez
(74) *Attorney, Agent, or Firm* — Harness, Dickey & Pierce, P.L.C.

(57) ABSTRACT

A controller changes a position and/or orientation of a treatment head by controlling an operation of a robot arm according to an external input. A probe driver changes a projection amount of a diagnostic probe with respect to an irradiator. Further, the controller performs synchronous control to synchronize the probe driver and the robot arm with each other so that the relative position between the irradiator and the distal end of the diagnostic probe changes while holding the distal end position of the diagnostic probe.

2 Claims, 10 Drawing Sheets

TREATMENT APPARATUS

CROSS REFERENCE TO RELATED APPLICATIONS

The present application is a continuation application of International Patent Application No. PCT/JP2019/011487 filed on Mar. 19, 2019, which designated the U.S. and claims the benefit of priority from Japanese Patent Application No. 2018-054209 filed on Mar. 22, 2018. The entire disclosures of all of the above applications are incorporated herein by reference.

TECHNICAL FIELD

The present disclosure relates to a treatment apparatus that performs treatment using a treatment head attached to a robot arm.

BACKGROUND

There is describes an ultrasound treatment apparatus having a treatment head attached to the distal end of a robot arm. In the ultrasound treatment apparatus, the treatment head includes (i) a diagnostic probe for ultrasound diagnosis and (ii) an irradiator for irradiation of focused ultrasound (hereinafter, HIFU). HIFU is an abbreviation for High Intensity Focused Ultrasound. The ultrasound treatment apparatus performs the treatment by observing the affected area of the patient using a diagnostic probe and irradiating the affected area with HIFU using the irradiator.

Then, at the treatment, the treatment head is moved relative to a treatment target, to perform the treatment while making the focus of the HIFU coincide with the affected area.

SUMMARY

According to an example of the present disclosure, a treatment apparatus is provided to include a robot arm, a treatment head, a controller, and a probe driver.

The robot arm has six degrees of freedom. The treatment head is provided at the distal end of the robot arm and has an irradiator and a diagnostic probe. The irradiator irradiates focused ultrasound. The diagnostic probe is provided so as to project from the center of the irradiator in the irradiation direction of the focused ultrasound. The diagnostic probe transmits and receives diagnostic ultrasound different from the focused ultrasound. The controller changes at least one of the position and the orientation of the treatment head by controlling the operation of the robot arm according to an input from the outside. The probe driver changes the projection amount of the diagnostic probe with respect to the irradiator.

Herein, the controller performs at least synchronous control for driving the probe driver and the robot arm in synchronization with each other so that the relative position between the irradiator and the distal end of the diagnostic probe changes while holding the distal end position of the diagnostic probe.

BRIEF DESCRIPTION OF DRAWINGS

The objects, features, and advantages of the present disclosure will become more apparent from the following detailed description made with reference to the accompanying drawings. In the drawings.

DETAILED DESCRIPTION

Hereinafter, an embodiment of the present disclosure will be described with reference to the drawings.

1. CONFIGURATION

Figure 1:
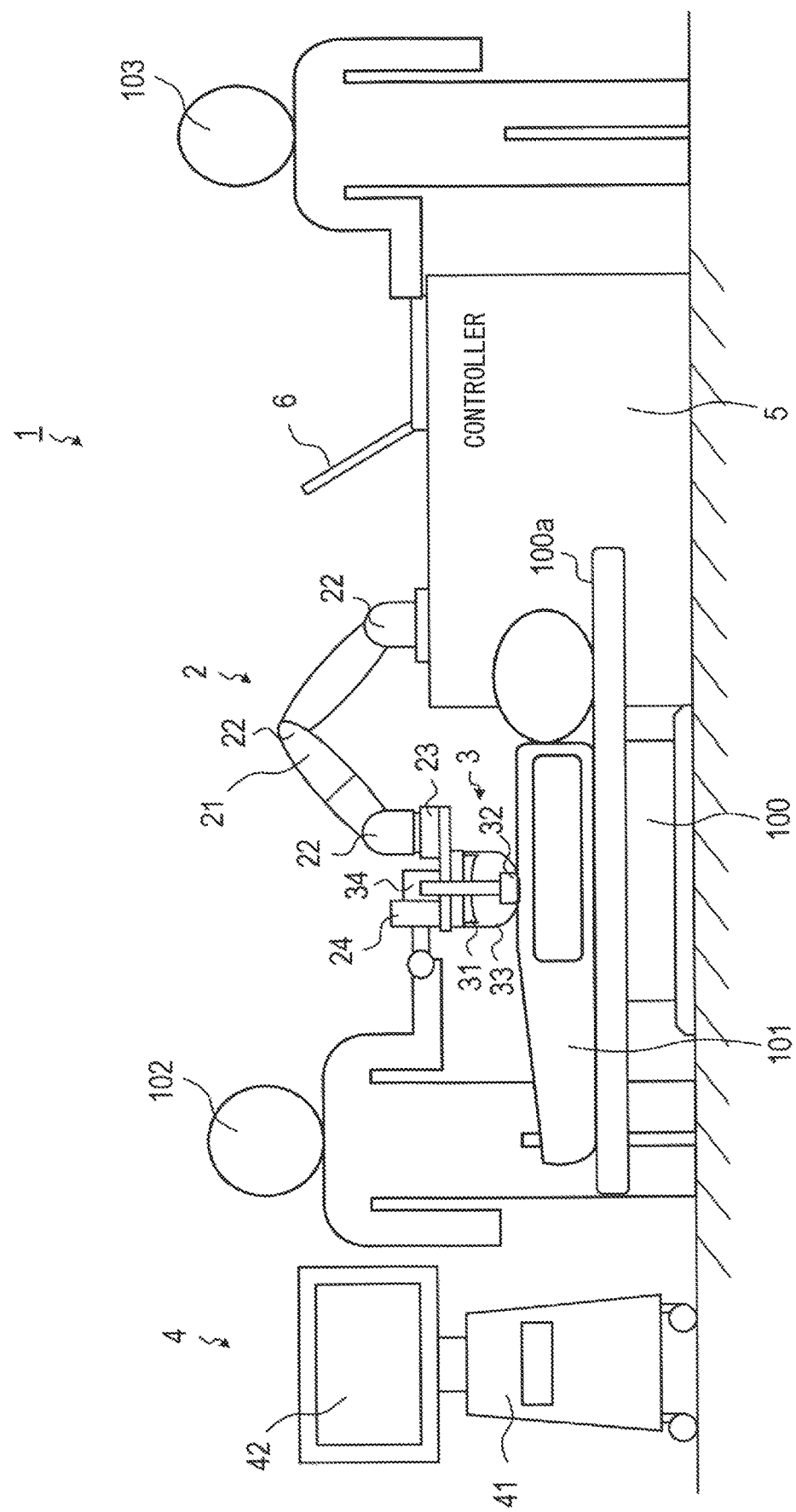
FIG. 1 is a schematic diagram showing an outline of a treatment apparatus.
Figure 2:
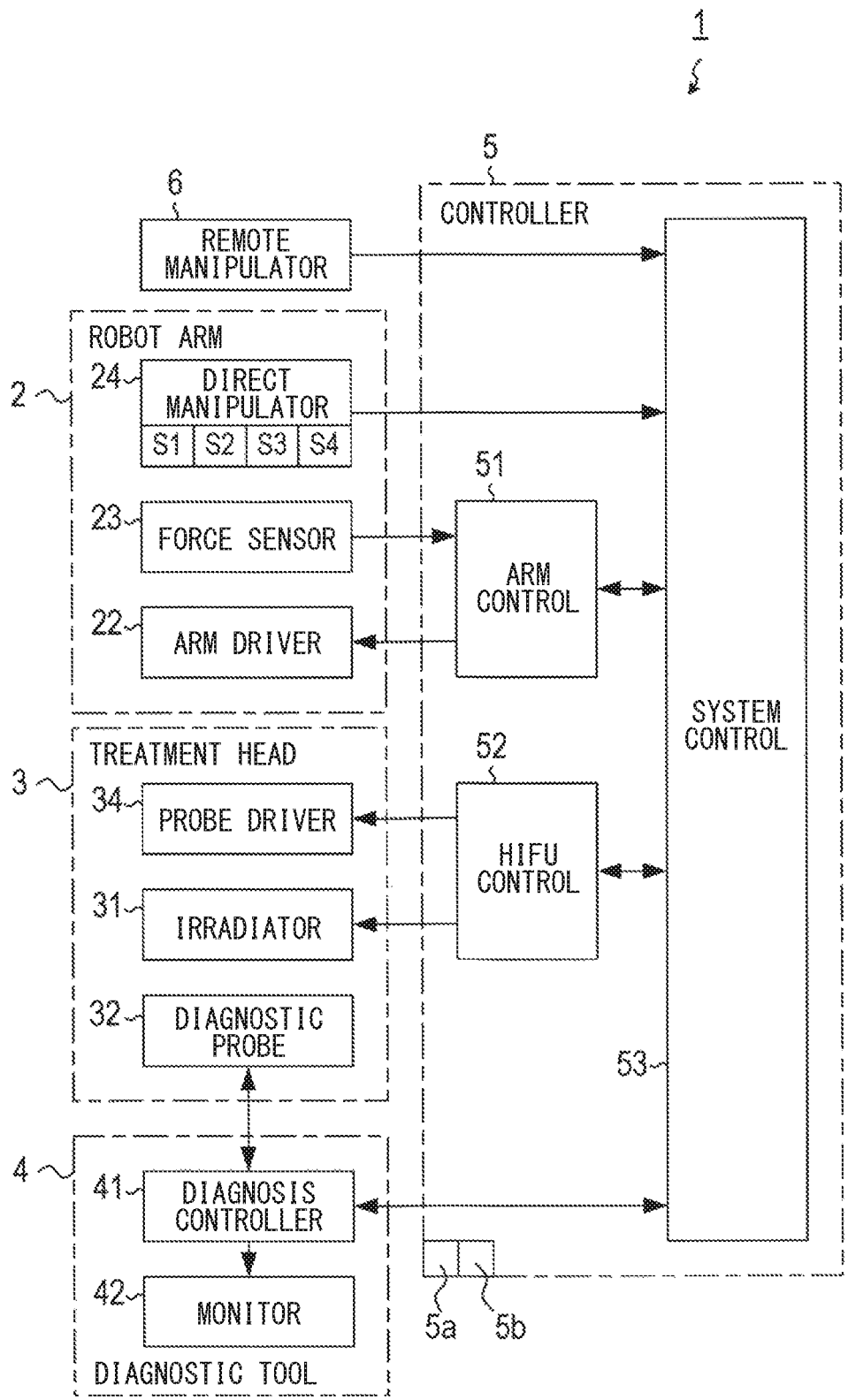
FIG. 2 is a block diagram showing a functional configuration of a treatment apparatus.

A treatment apparatus 1 shown in FIGS. 1 and 2 is an apparatus that performs treatment by irradiating a treatment target 101 supported by a treatment table 100 with a focused ultrasound (hereinafter, HIFU). HIFU is an abbreviation for High Intensity Focused Ultrasound. The treatment apparatus 1 includes a robot arm 2, a treatment head 3, an ultrasound diagnostic tool 4, a controller 5, and a remote manipulator 6. The remote manipulator 6 is an example of an instruction input unit or an instruction input interface.

[1-1. Treatment Head]

The treatment head 3 is an instrument that irradiates a treatment target 101 such as a patient with (i) an HIFU, which is ultrasound for treatment, and (ii) a diagnostic ultrasound, which is an ultrasound different from HIFU.

The treatment head 3 includes an irradiator 31, a diagnostic probe 32, a water bag 33, and a probe driver 34.

The irradiator 31 has an irradiation surface formed as a concave surface, and irradiates the HIFU toward one point serving as a focus. The distance from the irradiator 31 to the focus is constant.

The diagnostic probe 32 is a shaft-shaped member that projects from the center of the irradiation surface of the irradiator 31 in the irradiation direction of the HIFU. The diagnostic probe 32 transmits and receives diagnostic ultrasound at its distal end. The diagnostic probe 32 irradiates a diagnostic ultrasound toward a preset angular range centered on a direction in which the central axis (hereinafter, probe axis) is extended, that is, a projecting direction with respect to the irradiator 31. The diagnostic probe 32 thereby receives the reflected ultrasound.

The water bag 33 is a watertight bag that covers the irradiator 31 and the diagnostic probe 32. The water bag 33 is filled with water serving as a transmission medium of the HIFU in order to suppress the attenuation of the HIFU radiated from the irradiator 31. Further, both the examination and the treatment for the treatment target 101 are performed in a state where the water bag 33 of the treatment head 3 is in contact with the treatment target 101. In the water bag 33, usually, either (i) the part where the distal end of the diagnostic probe 32 comes into contact with the inside or (ii) the part located on the probe axis, comes into contact with the treatment target 101.

The probe driver 34 is an actuator that moves the diagnostic probe 32 along the probe axis. The probe driver 34 changes the projection amount (hereinafter referred to as probe position) of the diagnostic probe 32 with respect to the irradiator 31, and consequently the relative position of the diagnostic probe 32 with respect to the irradiator 31.

[1-2. Robot Arm]

The treatment head 3 is attached to the distal end of the robot arm 2. The robot arm 2 is used for controlling both the position and the orientation of the treatment head 3. The robot arm 2 includes a multi-joint arm 21, an arm driver 22, a force sensor 23, and a direct manipulator 24. The direct manipulator 24 is an example of an instruction input unit or an instruction input interface.

The multi-joint arm 21 has a plurality of links connected by a plurality of joints, and realizes movement in six degrees of freedom. The arm driver 22 has a plurality of motors installed at each joint of the multi-joint arm 21. The arm driver 22 changes the shape of the multi-joint arm 21 according to an instruction from the controller 5.

The force sensor 23 is provided at the distal end of the multi-joint arm 21. That is, the treatment head 3 is attached to the distal end of the multi-joint arm 21 (i.e., the distal end of the robot arm 2) via the force sensor 23. The force sensor 23 detects the magnitude and direction of the force transmitted to the robot arm 2 via the treatment head 3 and notifies the controller 5 of the detected magnitude and direction.

The direct manipulator 24 is provided adjacent to the distal end of the robot arm 2, and is gripped by a worker 102 when manually manipulating the robot arm 2. The direct manipulator 24 also has a plurality of switches S1 to S4 for inputting an instruction to the controller 5.

The plurality of switches include a manipulation changeover switch S1, a control changeover switch S2, an adjustment instruction switch S3, and a retraction instruction switch S4.

The manipulation changeover switch S1 is a switch manipulated when changing the manipulation mode of the robot arm 2 to either a manual mode or a remote mode. The manual mode is set when the robot arm 2 is manually manipulated. The remote mode is set when the robot arm 2 is remotely controlled via the remote manipulator 6.

The control changeover switch S2 is a switch manipulated when switching the control mode of the robot arm 2 to any one of a free mode, a plane limited mode, and a rotation limited mode. The free mode is a control mode in which at least one of the position and the orientation of the treatment head 3 can be freely changed. The plane limited mode is a control mode in which the movement of the treatment head 3 is limited to the movement on a designated plane set so as to include the base point. The rotation limited mode is a control mode in which the movement of the treatment head 3 is limited to the rotation movement about the base point. The base point is a point where the distal end of the diagnostic probe 32 is located at the time when the control mode is switched to the plane limited mode or the rotation limited mode.

The adjustment instruction switch S3 is a switch manipulated to input an adjustment instruction when adjusting the focus of the HIFU. The retraction instruction switch S4 is a switch manipulated to input a retraction instruction when the diagnostic probe 32 is moved to the retraction position where blocking of the HIFU by the diagnostic probe 32 is suppressed.

[1-3. Manipulator]

The remote manipulator 6 has a function necessary for remote control of the treatment apparatus 1, and is manipulated by an operator 103. Specifically, the remote manipulator 6 includes at least (i) the function of receiving the instruction inputs equivalent to the plurality of switches S1 to S4 provided by the direct manipulator 24 and (ii) the function of receiving the instruction input regarding the movement of the treatment head 3.

The remote manipulator 6 may be a dedicated device, or may be, for example, a general-purpose personal computer which installs an application required for remote control of the treatment apparatus 1.

[1-4. Ultrasound Diagnostic Tool]

The ultrasound diagnostic tool 4 includes a diagnosis controller 41 and a monitor 42.

The diagnosis controller 41 causes the diagnostic probe 32 to emit diagnostic ultrasound and image-processes the reflected wave received by the diagnostic probe 32 according to an instruction from the controller 5. By doing so, two-dimensional image data representing the internal state of the treatment target 101 is generated. The diagnosis controller 41 displays a diagnostic image on the monitor 42 based on the image data and supplies the image data to the controller 5.

Figure 10:
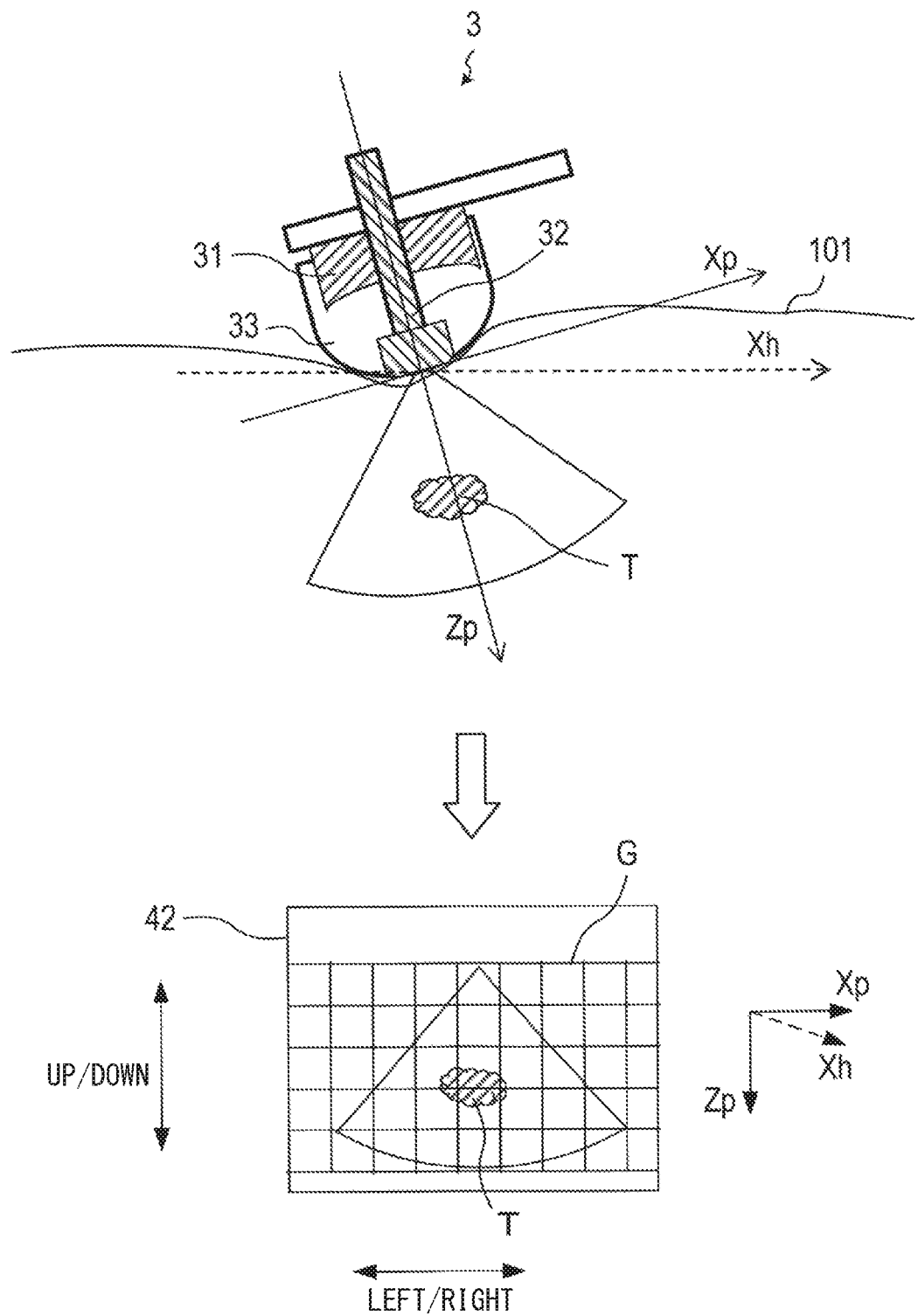
FIG. 10 is an explanatory diagram related to a diagnostic image.

In addition, as shown in FIG. 10, the diagnosis controller 41 displays on the monitor 42 a diagnostic image on which the grid G is superimposed with intervals according to the treatment accuracy due to the irradiation of HIFU from the irradiator 31. For example, if a treatment accuracy of 5 mm is required, a 5 mm square grid G is displayed on the monitor 42.

[1-5. Controller]

The controller 5 includes a microcomputer having a CPU 5a and a semiconductor memory (hereinafter, memory) 5b such as RAM or ROM. Each function of the controller 5 is implemented by the CPU 5a executing a program stored in the non-transitory tangible storage medium. In this example, the memory 5b corresponds to a non-transitory tangible storage medium storing the program. When the execution of the program, a method corresponding to the program is executed. The controller 5 may include one or more microcomputers.

The controller 5 includes an arm controller unit 51, an HIFU controller unit 52, and a system controller unit 53 as functional unit blocks. The technique for implementing the function of each controller unit included in the controller 5 is not limited to software, and a part or all of the function may be implemented by using one or a plurality of hardware circuits. For example, when the above-described function may be implemented by an electronic circuit which is hardware, the electronic circuit may be implemented by a digital circuit, an analog circuit, or a combination thereof.

The arm controller unit 51 drives the arm driver 22 according to the detection result of the force sensor 23 and the instruction from the system controller unit 53, and changes the shape of the multi-joint arm 21. Thus, at least one of the position and the orientation of the treatment head 3 is controlled. In addition, the arm controller unit 51 notifies the system controller unit 53 of the state of the robot arm 2 (hereinafter, arm state). Note that the arm controller unit 51 is given, as instructions from the system controller unit 53, (i) manipulation mode setting, (ii) control mode setting, (iii) adjustment instruction presence/absence, (iv) retraction instruction presence/absence, and (v) movement instruction of the treatment head 3. The arm controller unit 51 executes different drive processes for each control mode. The details will be described later.

When the manipulation mode is the manual mode, the arm controller unit 51 detects the magnitude and direction of the acting force applied to the robot arm 2 by a worker 102 with the force sensor 23, and generates a movement instruction requiring the movement of the treatment head 3, from the detection result. Then, the arm controller unit 51 calculates the control amount of each motor belonging to the arm driver 22 according to the generated movement instruction, and drives each motor.

Further, when the manipulation mode is the remote mode, the arm controller unit 51 acquires (i) the movement instruction of the treatment head 3 input from the remote manipulator 6 and notified via the system controller unit 53, or (ii) the movement instruction of the treatment head 3 calculated according to a preset program. Then, the arm controller unit 51 calculates the control amount of each motor belonging to the arm driver 22 according to the acquired movement instruction, and drives each motor.

It should be noted that the movement instruction of the treatment head 3 indicates the movement direction and the movement amount using the probe coordinate system. The probe coordinate system is a three-dimensional system in which (i) the distal end of the diagnostic probe 32, that is, the transmitting/receiving point of diagnostic ultrasound is the origin, (ii) the direction along the probe axis is the Z-axis direction and (iii) the plane orthogonal to the Z-axis is the XY plane. The X axis and the Y axis are set so that an image on the XZ plane is displayed on the monitor 42. Hereinafter, of the probe coordinate system, the X axis is represented by Xp, the Y axis is represented by Yp, and the Z axis is represented by Zp.

The HIFU controller unit 52 controls the radiation of the HIFU by the irradiator 31 according to the instruction from the system controller unit 53. Further, the HIFU controller unit 52 drives the probe driver 34 according to an instruction from the system controller unit 53 to change the probe position. Further, the HIFU controller unit 52 notifies the system controller unit 53 of the probe position.

The system controller unit 53 controls the display of the monitor 42 and the movements of the arm controller unit 51 and the HIFU controller unit 52, according to (i) an input from the remote manipulator 6 or an input from the switch groups S1 to S4 of the direct manipulator 24, (ii) the arm state from the arm controller unit 51, (iii) the probe position from the HIFU controller unit 52, and (iv) the image data from the diagnosis controller 41.

The system controller unit 53 executes at least a target display process, a focus display process, an instruction calculation process, and a mode switching process.

Figure 8:
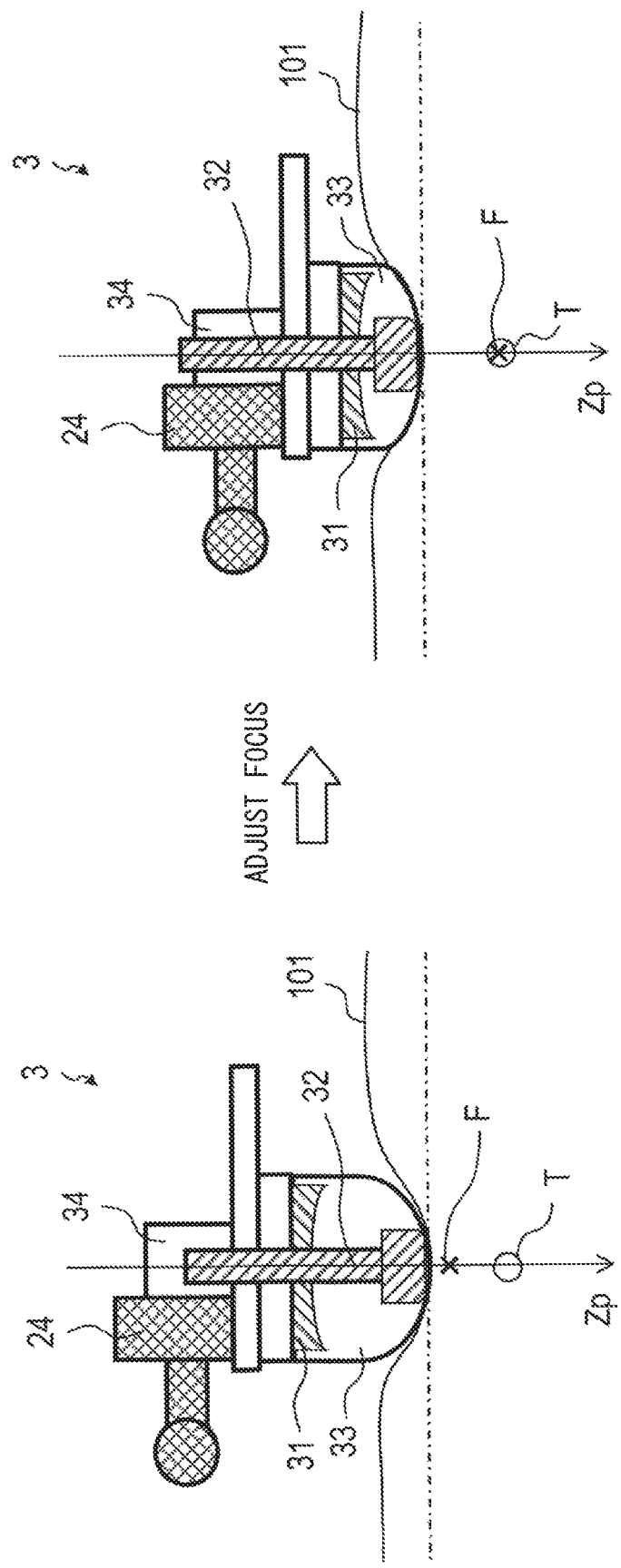
FIG. 8 is an explanatory diagram related to a focus adjustment control of HIFU.

As shown in FIGS. 8 and 10, the target display process sets a target range T including an affected area which is an irradiation target of the HIFU and notifies the diagnosis controller 41 of the set target range T. Thus the target range T is displayed on the diagnostic image of the monitor 42 in superimposition. The target range T may be, for example, (i) a region extracted as an affected area by image processing on the image data from the diagnosis controller 41, or (ii) a region set according to an input from the remote manipulator 6 after being confirmed by the monitor 42.

The focus display process calculates the focus position F of the HIFU from the arm state and the probe position, and notifies the diagnosis controller 41 of the calculated focus position F, thereby displaying the focus position F in superimposition on the diagnostic image on the monitor 42. Note that the focus display process may change the probe position in addition to the focus position F. A focus range (not shown) that is a range of possible focus positions may thereby be calculated and displayed on the monitor 42.

When the target range T is set, the instruction calculation process automatically generates a movement instruction for changing the arm state so that the probe axis passes through the center of the target range. The instruction calculation process is executed when (i) the manipulation mode is the remote mode and (ii) the setting is made to generate the movement instruction regardless of the input from the remote manipulator 6.

2. PROCESSES

[2-1. Mode Switching Process]

Figure 3:
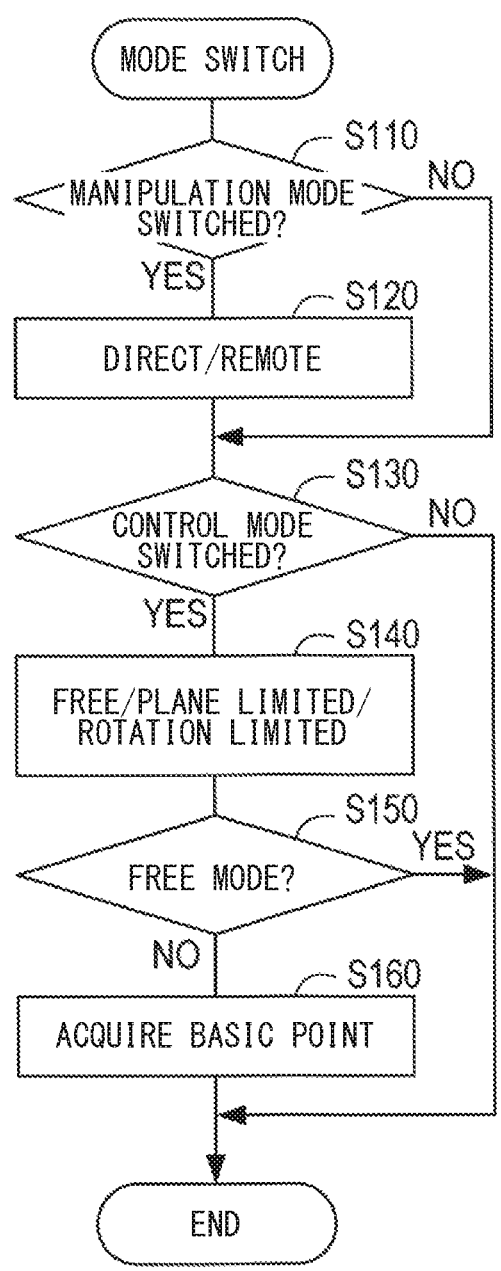
FIG. 3 is a flowchart of a mode switching process.

The mode switching process repeatedly executed by the system controller unit 53 will be described with reference to the flowchart of FIG. 3.

Note that, in the initial state, the diagnostic probe 32 is set to, for example, an intermediate position within a range that the probe position can take. The position is not limited to this, and may be set to the most projected position.

In S110, the system controller unit 53 determines whether the manipulation mode has been switched via the remote manipulator 6 or the direct manipulator 24. When it is determined that the manipulation mode has not been switched, the process is advanced to S120, and when it is determined that the manipulation mode has been switched, the process is advanced to S130.

In S120, the system controller unit 53 sets the manipulation mode to either the manual mode or the remote mode according to the contents of the switching operation performed, and advances the process to S130.

In S130, the system controller unit 53 determines whether the control mode has been switched via the remote manipulator 6 or the direct manipulator 24. When it is determined that the control mode has been switched, the process is advanced to S140, and when it is determined that the control mode has not been switched, the process is ended.

In S140, the system controller unit 53 sets the control mode to any one of the free mode, the plane limited mode, and the rotation limited mode in accordance with the content of the switching operation performed, and advances the process to S150.

In S150, the system controller unit 53 determines whether the control mode set in S140 is the free mode. When it is determined that the set control mode is the free mode, the process is ended. When it is determined that the set control mode is not the free mode but the plane limited mode or the rotation limited mode, the process is advanced to S160.

In S160, the system controller unit 53 acquires the position of the distal end of the diagnostic probe 32 as a base point, stores it in the memory 5*b*, and the process is ended.

[2-2. Free Mode]

Figure 4:
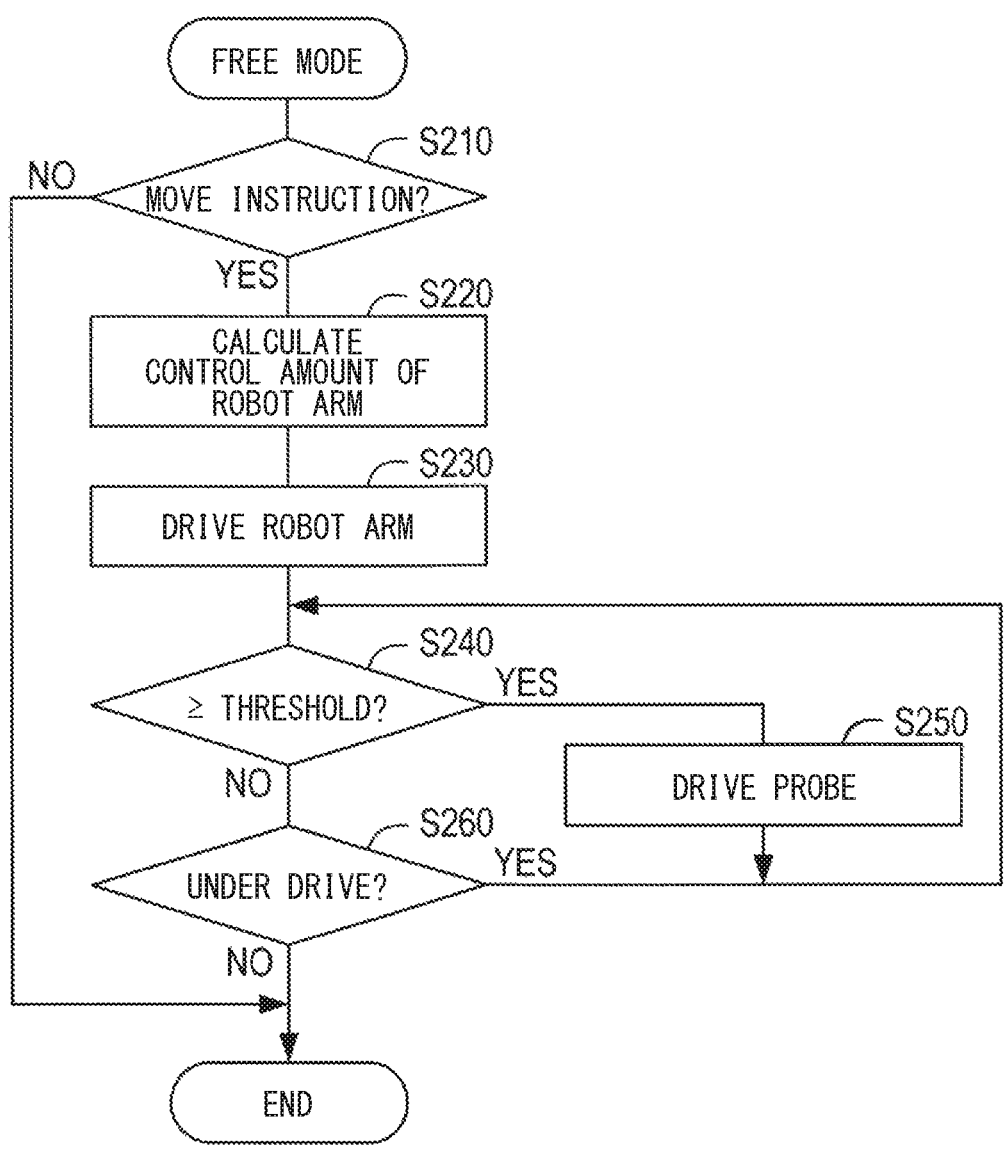
FIG. 4 is a flowchart of a drive process in a free mode.

The drive process repeatedly executed by the arm controller unit 51 when the control mode is the free mode will be described with reference to the flowchart of FIG. 4.

In S210, the arm controller unit 51 determines whether there is an input of a movement instruction for changing at least one of the position and the orientation of the treatment head 3. When it is determined that the movement instruction is input, the process is advanced to S220, and when it is determined that the movement instruction is not input, the process is ended. The movement instruction is calculated from the detection result of the force sensor 23 when the manipulation mode is the manual mode. In contrast, the movement instruction is input from the system controller unit 53 when the manipulation mode is the remote mode. The movement amount input from the system controller unit 53 may be input from the remote manipulator 6 or may be automatically generated by the instruction calculation process.

In S220, the arm controller unit 51 calculates the control amount of the robot arm 2, that is, the control amount of each motor belonging to the arm driver 22, based on the instruction input and the arm state.

In S230, the arm controller unit 51 drives the arm driver 22 according to the control amount calculated in S220 to change the arm state. Thus, at least one of the position and the orientation of the treatment head 3 is changed.

In S240, the arm controller unit 51 determines whether the force sensor 23 has detected a force equal to or higher than a preset pressure threshold value. The pressure threshold value is set in consideration of the degree of pain that occurs in the treatment target 101 when the treatment head 3 is pressed against the treatment target 101, and is set to a magnitude that does not cause pain to the treatment target 101, for example. When it is determined that the force equal to or higher than the pressure threshold value is detected, the process is advanced to S250, and when it is determined that the force equal to or higher than the pressure threshold value is not detected, the process is advanced to S260.

In S250, the arm controller unit 51 performs a synchronous control of driving the probe driver 34 via the HIFU controller unit 52 in synchronization with the arm driver 22 (that is, the movement of the robot arm 2). The process is then returned to S240. In this synchronous control, the probe driver 34 is driven so that the distal end of the diagnostic probe 32 moves by a predetermined amount in the direction approaching the irradiator 31. This reduces the pressing force of the treatment head 3 onto the treatment target 101.

In S260, the arm controller unit 51 determines whether the drive of the robot arm 2 based on the processing in S230 is completed. When it is determined that the drive has not ended, the process is returned to S240. When it is determined that the drive has ended, the process is ended.

Through the processing in S240 to S260, the probe position changes until the pressing force becomes less than or equal to the pressure threshold value. That is, it is possible to prevent the treatment target 101 from suffering pain due to a change in at least one of the position and the orientation of the treatment head 3.

[2-3. Plane Limited Mode]

Figure 5:
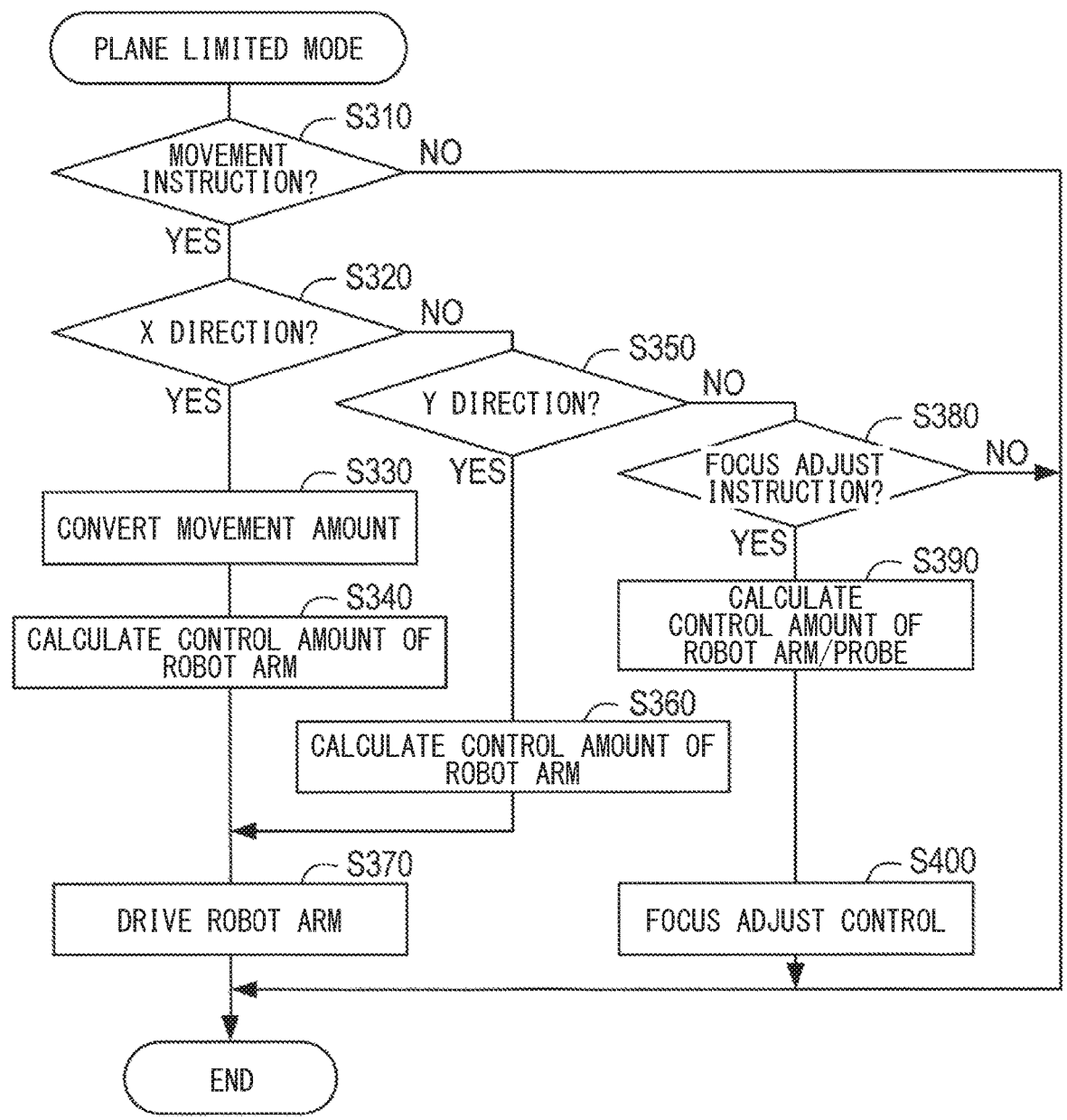
FIG. 5 is a flowchart of a drive process in a plane limited mode.

The drive process repeatedly executed by the arm controller unit 51 when the control mode is the plane limited mode will be described with reference to the flowchart of FIG. 5.

A designated plane is defined as a plane that includes the base point P acquired in S160 and is parallel to the support surface 100a that supports the treatment target 101 on the treatment table 100 that supports the treatment target 101.

In S310, the arm controller unit 51 determines whether a movement instruction for changing at least one of the position and the orientation of the treatment head 3 is input. Note that this determination is the same as in S110. When it is determined that the movement instruction has been input, the process is advanced to S320. When it is determined that the movement instruction has not been input, the process is ended.

In S320, the arm controller unit 51 determines whether the movement direction indicated by the movement instruction is the X-axis direction. When it is determined that the movement direction is the X-axis direction, the process is advanced to S330. When it is determined that the movement direction is not the X-axis direction, the process is advanced to S340.

In S330, the arm controller unit 51 converts the amount of movement $\Delta Xp$ in the X-axis direction of the probe coordinate system indicated by the movement instruction into the amount of movement $\Delta Xh$ in the X-axis direction on the designated plane using the equation (1). The process is then advanced to S350. Note that $\theta$ is the inclination of the designated plane in the X-axis direction with respect to the X-axis of the probe coordinate system.

$$\Delta Xh = \Delta Xp / \cos \theta \qquad (1)$$

In S340, the arm controller unit 51 calculates the control amount of the robot arm 2 using the movement amount $\Delta Xh$ calculated in S330, and advances the process to S370. Specifically, the control amount of the robot arm 2 is set so that the position of the treatment head 3 is moved by the movement amount $\Delta Xh$ in the X-axis direction of the designated plane while maintaining the orientation of the treatment head 3.

In S350, the arm controller unit 51 determines whether the movement direction indicated by the movement instruction is the Y-axis direction. When it is determined that the movement direction is the Y-axis direction, the process is advanced to S360. When it is determined that the movement direction is not the Y-axis direction, that is, when it is determined that the movement direction is the Z-axis direction, the process is advanced to S380.

In S360, the arm controller unit 51 calculates the control amount of the robot arm 2 using the movement amount $\Delta Yp$ in the Y-axis direction of the probe coordinate system indicated by the movement instruction, and advances the process to S370. Specifically, the control amount of the robot arm 2 is set so as to move the position of the treatment head 3 by $\Delta Yp$ in the Y-axis direction of the designated plane while maintaining the orientation of the treatment head 3.

In S370, the arm controller unit 51 drives the arm driver 22 according to the control amount of the robot arm calculated in S340 or S360 to change the arm state, thereby changing the position of the treatment head 3 and ending the process.

In S380, the arm controller unit 51 determines whether an adjustment instruction has been input. The adjustment instruction is input from either the adjustment instruction switch S3 or the remote manipulator 6. When it is determined that the adjustment instruction has not been input, the process is ended, and when it is determined that the adjustment instruction has been input, the process is advanced to S390.

In S390, the arm controller unit 51 calculates the control amount of the robot arm 2 using the movement amount $\Delta Zp$ in the Z-axis direction indicated by the movement instruction. Specifically, the control amount of the robot arm 2 is set so as to move the position of the treatment head 3 by the movement amount $\Delta Zp$ in the Z-axis direction of the probe coordinate system while maintaining the orientation of the treatment head 3. Further, the arm controller unit 51 calculates the control amount for changing the prove position in synchronization with the movement of the robot arm 2 in order that the distal end position of the diagnostic probe 32 on the designated plane does not change with respect to the movement of the treatment head 3 along the Z-axis direction.

In S400, the arm controller unit 51 performs a focus adjustment control, which is one of the synchronous controls for driving the arm driver 22 and the probe driver 34 in synchronization, according to the control amount of the robot arm 2 and the control amount of the probe position calculated in S390. Then, the process is ended.

By driving in S400, the probe position changes while the distal end position of the diagnostic probe 32 is fixed. As a result, as shown in FIG. 8, the HIFU focus position F in the treatment target 101 changes along the Z-axis direction.

[2-4. Rotation Limited Mode]

Figure 6:
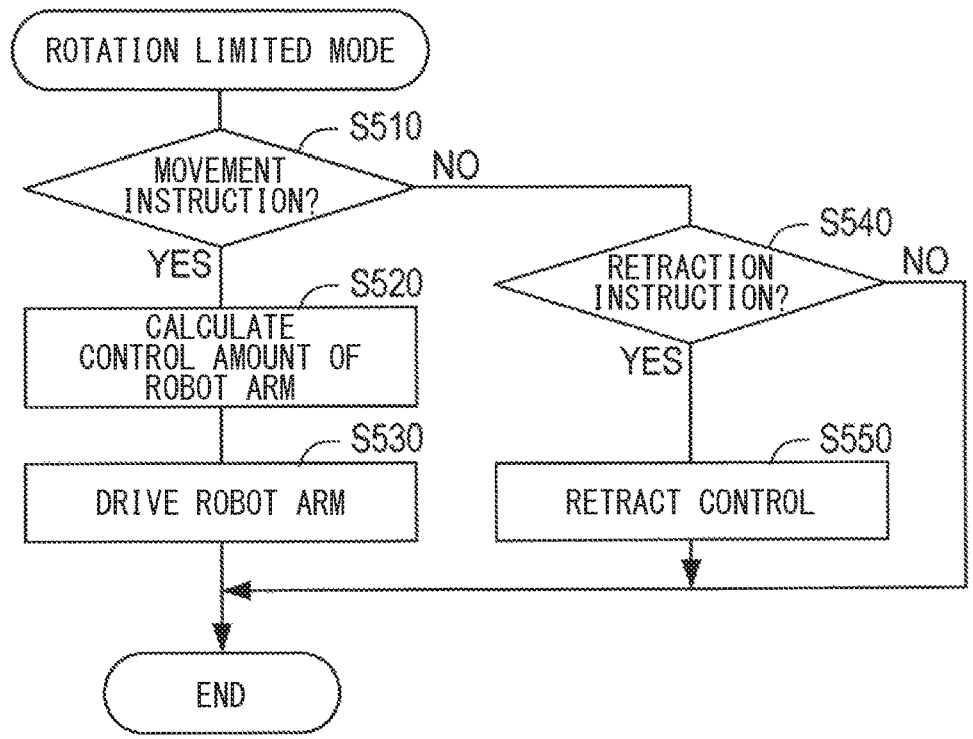
FIG. 6 is a flowchart of a drive process in a rotation limited mode.

The drive process repeatedly executed by the arm controller unit 51 when the control mode is the rotation limited mode will be described with reference to the flowchart of FIG. 6.

In S510, the arm controller unit 51 determines whether a movement instruction for changing at least one of the position and the orientation of the treatment head 3 is input. When it is determined that the movement instruction is input, the process is advanced to S520. When it is determined that the movement instruction is not input, the process is advanced to S540.

In S520, the arm controller unit 51 calculates the control amount of the robot arm 2 according to the movement amounts ΔXp and ΔYp indicated in the movement instruction. Specifically, the control amount of the robot arm 2 is to move the distal end of the robot arm 2 to which the treatment head 3 is attached along the spherical surface centered on the base point acquired in S160. Thus, the orientation of the treatment head 3 is set to be changed.

In S530, the arm controller unit 51 drives the arm driver 22 according to the control amount calculated in S530. As a result, the orientation of the treatment head 3 is changed, and the process is ended.

In S540, the arm controller unit 51 determines whether a retraction instruction has been input. The retraction instruction is input from either the retraction instruction switch S4 or the remote manipulator 6. When it is determined that the retraction instruction has not been input, the process is ended. When it is determined that the retraction instruction has been input, the process is advanced to S550.

In S550, the arm controller unit 51 executes the retraction control for driving the probe driver 34 so that the diagnostic probe 32 moves to the retraction position. This process is ended. The retraction position is set to a position moved toward the irradiator 31 from the probe position in the initial state.

3. OPERATION

Hereinafter, the operation of the treatment apparatus 1 will be described along a series of sequence from diagnosis to treatment. The manipulation mode may be either a manual mode or a remote mode, and the manipulation mode setting may be switched at any timing in the following procedure.

First, the worker 102 or the operator 103 sets the control mode to the free mode and causes the diagnostic probe 32 to transmit and receive diagnostic ultrasound. As a result, the diagnostic image is displayed on the monitor 42. The worker 102 or the operator 103 changes at least one of the position and the orientation of the treatment head 3 while checking the diagnostic image, and searches for a rough position of the affected area. At this time, the distal end of the treatment head 3, that is, the distal end of the diagnostic probe 32 is brought into contact with the treatment target 101, and a search is performed with a pressing force smaller than the pressure threshold value being applied. Note that when the pressing force on the treatment target 101 exceeds the pressure threshold value, the probe position is changed in the direction of decreasing the pressing force.

When the affected area is found, the worker 102 or the operator 103 switches the control mode from the free mode to the plane limited mode. At this time, the position of the distal end of the treatment head 3 in contact with the treatment target 101, that is, the position of the distal end of the diagnostic probe 32 is stored as the base point P.

In the plane limited mode, the movement of the treatment head 3 is limited to be on the designated plane. When the Z axis of the probe coordinate system (i.e., the probe axis) is aligned with the vertical direction of the ground coordinate system, the X-axis Xh of the designated plane on the monitor 42 matches the X-axis Xp of the probe coordinate system. In contrast, suppose a case where as shown in FIG. 10, the Z axis of the probe coordinate system is inclined with respect to the vertical direction of the ground coordinate system. In such a case, the X-axis Xh of the designated plane on the monitor 42 is inclined with respect to the X-axis direction Xp of the probe coordinate system.

Figure 7:
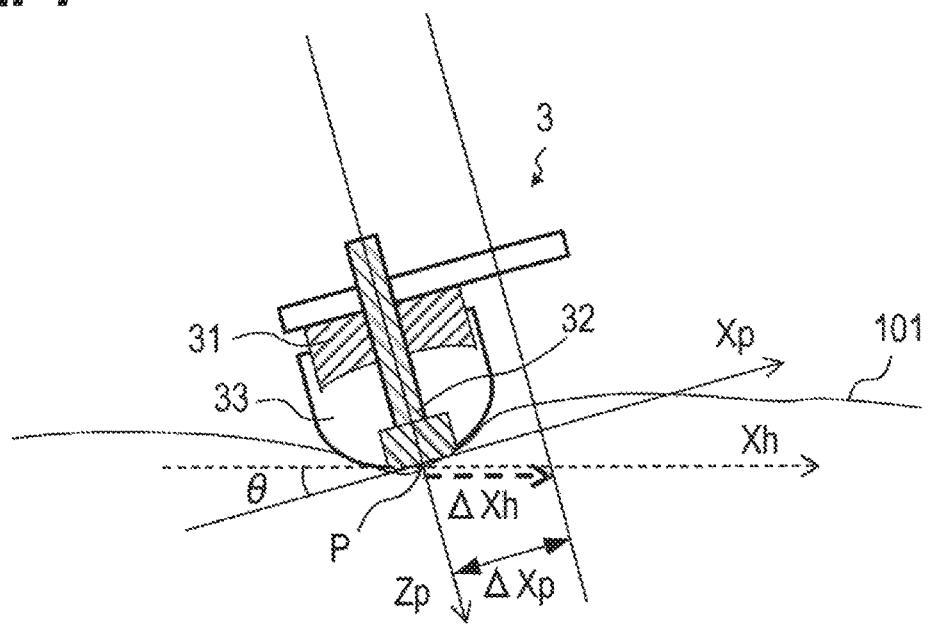
FIG. 7 is an explanatory diagram showing a relationship between an orientation of a treatment head and a movement amount in a horizontal limited mode.

In the plane limited mode, the movement instruction along the X-axis Xp direction of the probe coordinate system is converted into the movement of the designated plane in the X-axis Xh direction, and the movement amount is also converted into ΔXh. As shown in FIG. 7, the axis of the treatment head 3 when moving in the Xh direction by the converted movement amount ΔXh is set to match the Z axis of the treatment head 3 when moving in the Xp direction by the movement amount ΔXp before X conversion. That is, if the movement amount ΔXp is moved in the Xh direction without conversion, the treatment head 3 cannot be moved to a desired position (e.g., the front of the affected area) confirmed using the grid on the monitor 42. That is, the movement amount also needs to be converted in order to compensate for the error in the movement amount caused by the movement along the designated plane.

By using the plane limited mode, the treatment head 3 moves in the horizontal direction with respect to the treatment target 101 even if the orientation of the treatment head 3 is inclined. Therefore, it is possible to prevent the pressing force on the treatment target 101 from increasing with the movement of the treatment head 3 and from causing pain to the patient. In contrast, it is also possible to prevent the pressing force on the treatment target 101 from decreasing as the treatment head 3 moves, thereby preventing the affected area from being lost due to the movement of the internal organs.

The worker 102 or the operator 103 moves the treatment head 3 to the front of the affected area and then inputs a movement instruction in the Z-axis direction together with an adjustment instruction. Thus, the focus position of the HIFU is adjusted. At this time, as shown in FIG. 8, on the monitor 42, the target range T is displayed in front of the treatment head 3 and the focus position F of the HIFU is also displayed. Therefore, the movement amount in the Z-axis direction can be easily designated so that the focus position F overlaps the target range T.

After that, treatment is performed by causing the irradiator 31 to irradiate with HIFU.

The following will describe a case where the affected area is inside the ribs and the affected area is diagnosed or treated from between the ribs.

First, as in the case described above, the control mode is set to the free mode, and the diagnostic probe 32 is caused to transmit and receive diagnostic ultrasound to display a diagnostic image on the monitor 42. The worker 102 or the operator 103 changes at least one of the position and the orientation of the treatment head 3 while looking at the diagnostic image to search for the affected area.

When the affected area is found, the worker 102 or the operator 103 adjusts at least one of the position and the orientation of the treatment head 3 so that the affected area is located in front of the treatment head 3. Then, the control mode is switched to the rotation restriction mode. Note that before switching the control mode from the free mode to the rotation limited mode, the control mode may be temporarily switched to the plane limited mode. In this case, after performing at least one of the fine adjustment of the position and the adjustment of the focus position, the control mode may be switched to rotation limited mode. In any case, the position of the distal end of the diagnostic probe 32 at the time of switching to the rotation limited mode is stored as the base point.

Figure 9:
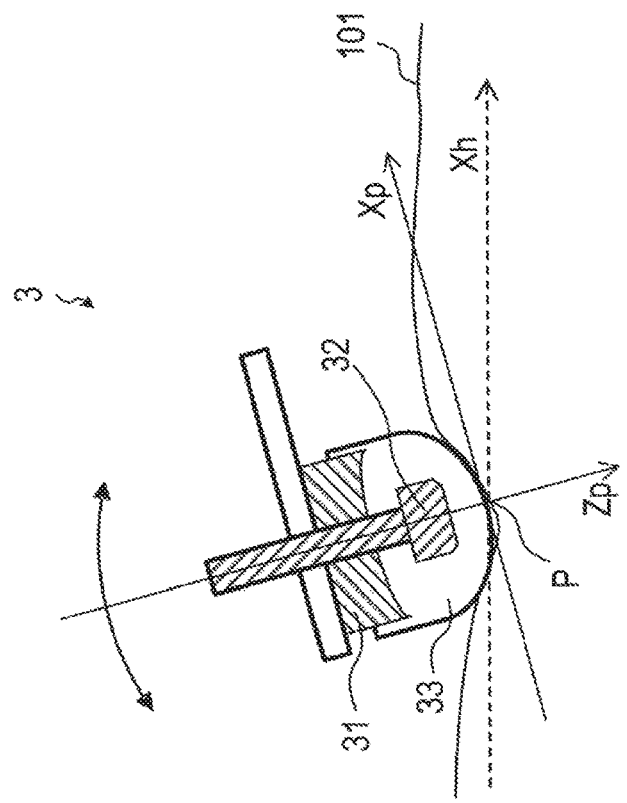
FIG. 9 is an explanatory diagram related to a withdrawal control of a diagnostic probe.
Figure 9:
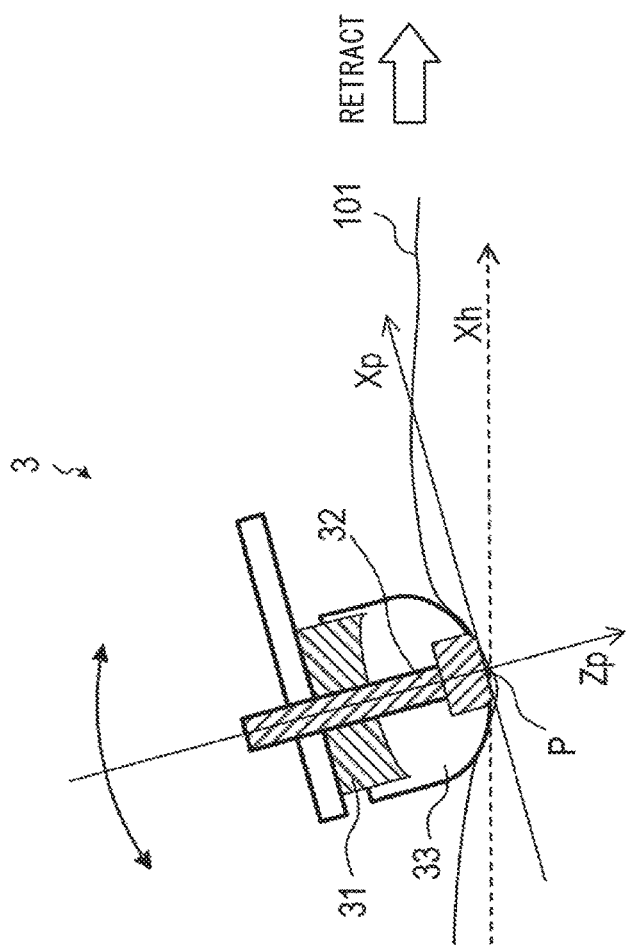

Next, the worker 102 or the operator 103 inputs a retraction instruction. As a result, as shown in FIG. 9, only the diagnostic probe 32 is moved to the retraction position while maintaining both the position and the orientation of the treatment head 3. As a result, it is possible to prevent the HIFU passing through the intercostal space from being blocked by the diagnostic probe 32.

After that, the worker 102 or the operator 103 inputs the movement instruction to change the orientation of the treatment head 3 around the base point P and causes the irradiator 31 to irradiate with HIFU to perform the treatment.

In this case, since the affected area is inside the ribs, even if the pressing force by the diagnostic probe 32 is removed, the state around the affected area does not change, and accurate treatment is realized.

4. EFFECTS

According to the first embodiment described in detail above, the following effects are obtained.

(1) In the treatment apparatus 1, in the plane limited mode, when an adjustment instruction and a movement instruction i the Z axis are input, synchronous control is performed to change the probe position while holding the distal end position of the diagnostic probe 32 as a base point. Therefore, without changing the state of the internal organs of the treatment target 101, the focus position of the HIFU can be adjusted appropriately.

(2) In the treatment apparatus 1, in the free mode, synchronous control is performed to change the probe position of the diagnostic probe 32 while holding the distal end position of the diagnostic probe 32 so that the pressing force of the diagnostic probe 32 on the treatment target 101 becomes smaller than a pressure threshold value. Therefore, even if the treatment head 3 is strongly pressed against the treatment target 101 for some reason, it is possible to prevent the treatment target 101 from suffering pain.

(3) In the treatment apparatus 1, the distal end position of the diagnostic probe 32 when the control mode is switched from the free mode to the plane limited mode or the rotation limited mode is set as the base point P. In the plane limited mode or the rotation limited mode, the movement of the robot arm 2 is limited to the movement constrained to the base point P.

Particularly, in the plane limited mode, the movement of the treatment head 3 is limited to the movement along the designated plane including the base point P. Therefore, even if the orientation of the treatment head 3 is inclined, it is possible to suppress an increase or decrease in the pressing force on the treatment target 101 as the treatment head 3 moves. As a result, it is possible to prevent the pressing force from increasing with the movement of the treatment head 3 to cause pain to the treatment target 101. Further, conversely, it is possible to prevent the affected area from being lost due to the decrease in the pressing force with the movement of the treatment head 3 and the movement of the internal organs.

In the rotation limited mode, the movement of the treatment head 3 is limited to the rotation around the base point P. Therefore, it is possible to easily change the irradiation direction of the HIFU while holding the contact portion between the treatment head 3 and the treatment target 101 in the intercostal space or the like. The treatment can be performed efficiently.

(4) In the treatment apparatus 1, in the plane limited mode, not only the movement direction of the treatment head 3 is converted, but also the movement amount is also converted so as to compensate an error in the movement amount caused by the difference between the movement instruction according to the probe coordinate system and the actual movement direction. Therefore, even when the movement instruction is generated based on the display of the monitor 42 according to the probe coordinate system, the position of the treatment head 3 can be accurately controlled.

(5) In the treatment apparatus 1, the retraction instruction is input in the rotation limited mode. As a result, the diagnostic probe 32 is moved to the retraction position while maintaining both the position and the orientation of the treatment head 3. Therefore, even when the HIFU is radiated via the intercostal space, the affected area can be efficiently irradiated with the HIFU without being blocked by the diagnostic probe 32.

5. OTHER EMBODIMENTS

Although the embodiment of the present disclosure has been described above, the present disclosure is not limited to the above-described embodiment, and various modifications can be implemented.

Figure 11:
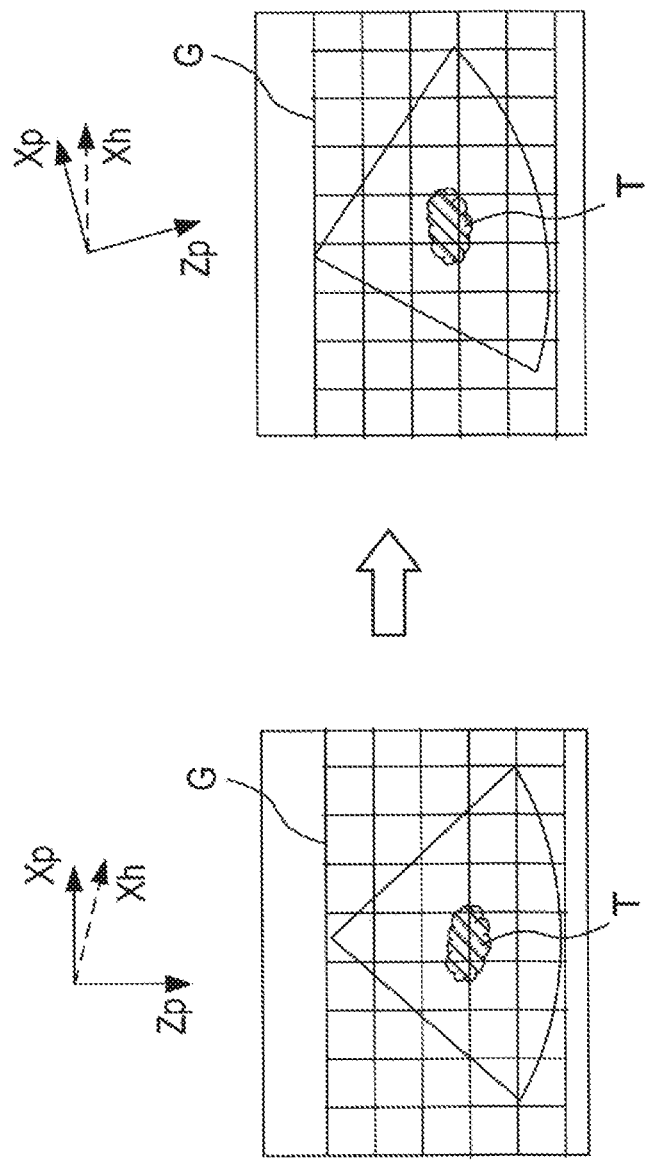
FIG. 11 is an explanatory diagram of a diagnostic image according to another embodiment.

(a) In the above embodiment, the monitor 42 displays the Z axis in the vertical direction of the screen and the X axis in the horizontal direction of the screen according to the probe coordinate system. However, the present disclosure is not limited thereto. For example, when the control mode is the plane limited mode, as shown in FIG. 11, the image may be inclined and displayed on the monitor so that the X axis of a limited coordinate plane matches the horizontal direction of the screen. In this case, the amount of movement in the X-axis direction read from the monitor and the amount of movement in the X-axis direction on the limited coordinate plane match, so the amount of movement can be used for control without conversion.

(b) In the above embodiment, the support surface 100a of the treatment table 100 on which the treatment target 101 is supported matches the horizontal plane of the ground coordinate system. However, the present disclosure is not limited thereto. For example, the support surface 100a may match the vertical plane of the ground coordinate system in order to support only the arm of the patient as the treatment target 101.

(c) In the above embodiment, the synchronous control for making the pressing force on the treatment target 101 smaller than the pressure threshold value is performed only in the free mode, but may be performed in another control mode.

(d) A plurality of functions of one element in the above embodiments may be implemented by a plurality of elements, or one function of one element may be implemented by a plurality of elements. Further, a plurality of functions of a plurality of elements may be implemented by one element, or one function implemented by a plurality of elements may be implemented by one element. In addition, a part of the configuration of the above embodiment may be omitted. At least a part of the configuration of the above embodiment may be added to or substituted for the configuration of the other above embodiment.

(e) The present disclosure can be realized in various forms, in addition to the treatment apparatus 1 described above, such as a system including the treatment apparatus 1 as a component, a program for causing a computer to function as the controller 5 in the treatment apparatus 1, a non-transitory tangible storage medium such as a semiconductor memory storing the program, or a control method of a robot arm.

For reference to further explain features of the present disclosure, the description is added as follows.

There is describes an ultrasound treatment apparatus having a treatment head attached to the distal end of a robot arm. In the ultrasound treatment apparatus, the treatment head includes (i) a diagnostic probe for ultrasound diagnosis and (ii) an irradiator for irradiation of focused ultrasound (hereinafter, HIFU). HIFU is an abbreviation for High Intensity Focused Ultrasound. The ultrasound treatment apparatus performs the treatment by observing the affected area of the patient using a diagnostic probe and irradiating the affected area with HIFU using the irradiator.

Then, at the treatment, the treatment head is moved relative to a treatment target, to perform the treatment while making the focus of the HIFU coincide with the affected area.

Detailed examination by the inventors have found issues as follows.

That is, in general, the affected area is observed while the patient is held down by the diagnostic probe in order to suppress the movement of organs due to respiration. However, when the treatment head is moved toward or away from the patient for focus adjustment after finding the affected area, the pressing state of the diagnostic probe changes. When the pressing force decreases, the state of the organ changes, possibly losing the affected area. In contrast, when the pressing force increases, the patient may suffer.

It is thus desired to provide a technique that facilitates precise robot manipulation according to the scene of treatment.

An aspect of the present disclosure described herein is set forth in the following clauses.

According to an aspect of the present disclosure, a treatment apparatus is provided to include a robot arm, a treatment head, a controller, and a probe driver.

The robot arm has six degrees of freedom. The treatment head is provided at the distal end of the robot arm and has an irradiator and a diagnostic probe. The irradiator irradiates focused ultrasound. The diagnostic probe is provided so as to project from the center of the irradiator in the irradiation direction of the focused ultrasound. The diagnostic probe transmits and receives diagnostic ultrasound different from the focused ultrasound. The controller changes at least one of the position and the orientation of the treatment head by controlling the operation of the robot arm according to an input from the outside. The probe driver changes the projection amount of the diagnostic probe with respect to the irradiator.

Herein, the controller performs at least synchronous control for driving the probe driver and the robot arm in synchronization with each other so that the relative position between the irradiator and the distal end of the diagnostic probe changes while holding the distal end position of the diagnostic probe.

With such a configuration, the position of the irradiator can be changed while holding the distal end position of the diagnostic probe. Thus accurate robot manipulation can be easily realized according to the scene of treatment. For example, while the pressing force to the treatment target by the diagnostic probe is maintained, the focused ultrasound can be focused and the increase of the pressing force to the treatment target can be suppressed.

What is claimed is:

1. A treatment apparatus comprising:

a robot arm having six degrees of freedom;

a treatment head provided at a distal end of the robot arm to include (i) an irradiator configured to irradiate with focused ultrasound, and (ii) a diagnostic probe provided to project from a center of the irradiator in an irradiation direction of the focused ultrasound, the diagnostic probe being configured to transmit and receive diagnostic ultrasound different from the focused ultrasound;

a controller configured to change (i) a position of the treatment head, or (ii) an orientation of the treatment head, or (iii) the position and the orientation of the treatment head by controlling a movement of the robot arm according to an input from an outside;

a probe driver configured to change a projection amount of the diagnostic probe with respect to the irradiator; and a force sensor configured to detect a direction and magnitude of a force applied to the treatment head, wherein:

the controller is configured to perform a synchronous control that drives the probe driver and the robot arm in synchronization with each other, the synchronous control in which a relative position between the irradiator and a distal end of the diagnostic probe is changed while the distal end of the diagnostic probe is maintained unchanged; and in response to that a pressing force on a treatment target detected by the force sensor along with a movement of the robot arm is equal to or greater than a preset pressure threshold value, the controller is configured to perform the synchronous control in which the pressing force is reduced to be smaller than the preset pressure threshold value.

2. The treatment apparatus according to claim 1, further comprising:

a manipulator configured to input at least an adjustment instruction to require an adjustment of the focus of the focused ultrasound, wherein:

the controller is configured to perform the synchronous control in response to (i) that an adjustment instruction is input from the manipulator and (ii) the input adjustment instruction is to require a change of the position of the treatment head along a projection direction of the diagnostic probe.

* * * * *